(12) United States Patent
Cha et al.

(10) Patent No.: US 8,975,369 B2
(45) Date of Patent: Mar. 10, 2015

(54) PROTEIN SKELETAL MODULE WHICH INCREASES THE BINDING AFFINITY AND BINDING SPECIFICITY OF ACTIVE POLYPEPTIDES

(71) Applicant: Kyungpook National University Industry—Academic Cooperation Foundation, Daegu (KR)

(72) Inventors: Kiweon Cha, Daegu (KR); In-Seop So, Daegu (KR); Soyoun Kim, Daegu (KR); Byung-Heon Lee, Daegu (KR); In San Kim, Daegu (KR)

(73) Assignee: Kyungpook National Univrsity Industry-Academic Cooperation Foundation, Daegu (KR)

( * ) Notice: Subject to any disclaimer, the term of this patent is extended or adjusted under 35 U.S.C. 154(b) by 0 days.

(21) Appl. No.: 14/057,654

(22) Filed: Oct. 18, 2013

(65) Prior Publication Data

US 2014/0079643 A1   Mar. 20, 2014

Related U.S. Application Data

(63) Continuation of application No. PCT/KR2012/002958, filed on Apr. 18, 2012.

(30) Foreign Application Priority Data

Apr. 18, 2011 (KR) .................. 10-2011-0035613

(51) Int. Cl.
| | | |
|---|---|---|
| *A61K 38/00* | (2006.01) | |
| *C07K 7/00* | (2006.01) | |
| *C07K 14/485* | (2006.01) | |
| *C07K 14/705* | (2006.01) | |
| *G01N 33/68* | (2006.01) | |
| *C07K 14/47* | (2006.01) | |
| *C07K 14/54* | (2006.01) | |

(52) U.S. Cl.
CPC ............. *C07K 14/485* (2013.01); *C07K 14/705* (2013.01); *G01N 33/68* (2013.01); *C07K 14/47* (2013.01); *C07K 14/5406* (2013.01); *C07K 2319/00* (2013.01)
USPC ........................................ 530/324; 514/21.3

(58) Field of Classification Search
None
See application file for complete search history.

(56) References Cited

U.S. PATENT DOCUMENTS

2003/0232013 A1* 12/2003 Sieckman et al. ........... 424/1.69
2003/0235882 A1* 12/2003 Shimkets et al. ............ 435/69.1

OTHER PUBLICATIONS

International Search Report issued on Nov. 21, 2012 in International Application No. PCT/KR2012/002958.
Park et al., "Epidermal growth factor-like domain repeat of stabilin-2 recognizes phosphatidylserine during cell corpse clearance", Molecular and Cellular Biology, vol. 28, No. 17, pp. 5288-5298, Sep. 2008.
Erlanson et al., "The leucine zipper domain controls the orientation of AP-1 in the NFAT-AP-1-DNA complex", Chemistry & Chemical Biology, vol. 3, pp. 981-991, Dec. 1996.
Park et al., "Stabilin-1 mediates phosphatidylserine-dependent clearance of cell corpses in alternatively activated macrophages", Journal of Cell Science, vol. 122, pp. 3365-3373, 2009.
Prevo et al., "Rapid plasma membrane-endosomal trafficking of the lymph node sinus and high endothelial venule scavenger receptor/homing receptor stabilin-1 (FEEL-CLEVER-1)", The Journal of Biological Chemistry, vol. 279, No. 50, pp. 52580-52592, Dec. 10, 2004.
Hulo, et al."The 20 years of PROSITE", Nucleic Acids Research vol. 36, pp. D245-D249, published online Nov. 14, 2007.
Letunic et al., "SMART 5:domains in the context of genomes and networks", Nucleic Acids Research vol. 34, pp. D257-D260, published in 2006.

* cited by examiner

*Primary Examiner* — James H Alstrum Acevedo
*Assistant Examiner* — Jeanette Lieb
(74) *Attorney, Agent, or Firm* — H.C. Park & Associates, PLC

(57) ABSTRACT

The present invention relates to a novel protein skeletal module which increases the binding affinity or binding specificity of active polypeptides. More particularly, the present invention relates to a protein skeletal module comprising polypeptides consisting of the $1^{st}$ to $19^{th}$ amino acids of the amino acid sequence expressed in sequence number 1; polypeptides comprising active polypeptides; and polypeptides consisting of the $29^{th}$ to $86^{th}$ amino acids of the amino acid sequence expressed in sequence number 1. The present invention also relates to a method for preparing the protein skeletal module. The protein skeletal module of the present invention increases the binding affinity or binding specificity of active polypeptides embedded therein, and therefore is effective in diagnosing and treating diseases.

7 Claims, 6 Drawing Sheets
(5 of 6 Drawing Sheet(s) Filed in Color)

DMID AP-1
( 1uM −0.063uM )

Peptide AP-1
(100uM − 6.25uM )

Negative control
(1uM-0.063uM)

SEQUENCE LISTING

<160> NUMBER OF SEQ ID NOS: 6

<210> SEQ ID NO 1
<211> LENGTH: 86
<212> TYPE: PRT
<213> ORGANISM: Artificial Sequence
<220> FEATURE:
<223> OTHER INFORMATION: DMID(Designed Modular Immunodiagnostics)
      cassette

<400> SEQUENCE: 1

Thr Ala Ile Asn Ala Cys Glu Ile Ser Asn Gly Gly Cys Ser Ala Lys
 1               5                  10                  15

Val Asp Cys Lys Arg Thr Thr Pro Gly Arg Arg Val Cys Thr Cys Lys
             20                  25                  30

Leu Gly Tyr Thr Gly Asp Gly Ile Val Cys Leu Glu Ile Asn Pro Cys
         35                  40                  45

Leu Glu Asn His Gly Gly Cys Asp Lys Asn Ala Glu Cys Thr Gln Thr
     50                  55                  60

Gly Pro Asn Gln Ala Ala Cys Asn Cys Leu Pro Ala Tyr Thr Gly Asp
65                  70                  75                  80

Gly Lys Val Cys Thr Leu
                85

<210> SEQ ID NO 2
<211> LENGTH: 260
<212> TYPE: DNA
<213> ORGANISM: Artificial Sequence
<220> FEATURE:
<223> OTHER INFORMATION: DMID(Designed Modular Immunodiagnostics)
      cassette

<400> SEQUENCE: 2
acagcaatca atgcctgtga gatcagcaat ggaggttgct ctgccaaggt cgactgtaag      60
agaaccaccc caggaaggcg agtgtgcacg tgcaagcttg gctacacggg tgatggcatt     120
gtgtgcctgg aaatcaaccc gtgtttggag aaccatggtg gctgtgacaa gaatgcggag     180
tgcacacaga caggacccaa ccaggctgcc tgtaactgtt tgccagcata cactggagat     240
ggaaaggtct gcacactcta                                                 260

<210> SEQ ID NO 3
<211> LENGTH: 6
<212> TYPE: PRT
<213> ORGANISM: Artificial Sequence
<220> FEATURE:
<223> OTHER INFORMATION: AP-1

<400> SEQUENCE: 3

Lys Arg Leu Asp Arg Asn
 1               5

<210> SEQ ID NO 4
<211> LENGTH: 254
<212> TYPE: DNA
<213> ORGANISM: Artificial Sequence
<220> FEATURE:
<223> OTHER INFORMATION: DMID(Designed Modular Immunodiagnostics)
      cassette with AP-1

<400> SEQUENCE: 4
acagcaatca atgcctgtga gatcagcaat ggaggttgct ctgccaaggt cgactgtcgt      60
aaacggctcg acaggaactg cacgtgcaag cttggctaca cgggtgatgg cattgtgtgc     120

```
ctggaaatca acccgtgttt ggagaaccat ggtggctgtg acaagaatgc ggagtgcaca      180
cagacaggac ccaaccaggc tgcctgtaac tgtttgccag catacactgg agatggaaag      240
gtctgcacac tcta                                                        254

<210> SEQ ID NO 5
<211> LENGTH: 260
<212> TYPE: DNA
<213> ORGANISM: Artificial Sequence
<220> FEATURE:
<223> OTHER INFORMATION: DMID(Designed Modular Immunodiagnostics)
      cassette with AP-1-6

<400> SEQUENCE: 5
acagcaatca atgcctgtga gatcagcaat ggaggttgct ctgccaaggt cgactgtaaa       60
cggctcgaca ggaacaggcg agtgtgcacg tgcaagcttg gctacacggg tgatggcatt      120
gtgtgcctgg aaatcaaccc gtgtttggag aaccatggtg gctgtgacaa gaatgcggag      180
tgcacacaga caggacccaa ccaggctgcc tgtaactgtt tgccagcata cactggagat      240
ggaaaggtct gcacactcta                                                  260

<210> SEQ ID NO 6
<211> LENGTH: 287
<212> TYPE: DNA
<213> ORGANISM: Artificial Sequence
<220> FEATURE:
<223> OTHER INFORMATION: DMID(Designed Modular Immunodiagnostics)
      cassette with AP-1-12

<400> SEQUENCE: 6
acagcaatca atgcctgtga gatcagcaat ggaggttgct ctgccaaggt cgactgtaag       60
agaacccgat tcctgaaacg gctcgacagg aacctctggg gcaggcgagt gtgcacgtgc      120
aagcttggct acacgggtga tggcattgtg tgcctggaaa tcaacccgtg tttggagaac      180
catggtggct gtgacaagaa tgcggagtgc acacagacag gacccaacca ggctgcctgt      240
aactgtttgc cagcatacac tggagatgga aaggtctgca cactcta                    287
```

PROTEIN SKELETAL MODULE WHICH INCREASES THE BINDING AFFINITY AND BINDING SPECIFICITY OF ACTIVE POLYPEPTIDES

CROSS-REFERENCE TO RELATED APPLICATIONS

This application is the continuation of International Application PCT/KR2012/002958, filed on Apr. 18, 2012, and claims priority from and the benefit of Korean Patent Application No. 10-2011-0035613, filed on Apr. 18, 2011, both of which are incorporated herein by reference in their entireties for all purposes as if fully set forth herein.

BACKGROUND

1. Field

The present invention relates to a novel protein skeletal module (scaffold protein) which increases binding affinity or binding specificity of an active polypeptide thereof, and more particularly, to a scaffold protein comprising an active polypeptide, the scaffold protein comprising: a) a polypeptide consisting of the $1^{st}$ to the $19^{th}$ amino acid residues of an amino acid sequence represented by SEQ ID NO: 1; b) a polypeptide including an active polypeptide; and c) a polypeptide consisting of the $29^{th}$ to the $86^{th}$ amino acid residues of the amino acid sequence represented by SEQ ID NO: 1, and a method for preparing the same.

2. Discussion of the Background

According to analysis on amino acid sequences and secondary and tertiary structures of proteins, many proteins are composed of independent domains or modules. The domain is a structurally and functionally independent unit. One or more of the same domains may be distributed in various proteins, and one protein may be composed of several domains. Specific information about domains can be found on websites for bioinformatics, such as Prosite (Hulo N etc., Nucleic Acids Res, 36:D245-249, 2008; Website: http://kr.expasy.org/prosite/) and SMART (Letunic I etc., Nucleic Acids Res, 34:D257-D260, 2006; Website: http://smart.embl-heidelberg.de/).

Intermolecular interactions (e.g., protein-protein interactions, protein-nucleic acid interactions, etc.) perform important functions in various life phenomena, such as growth, differentiation, and development of cells, intercellular/intracellular signaling, and mass transfer. In the related art, antibodies (full-length antibodies or their fragments) have been dominantly developed as molecules that specifically bind to target molecules to regulate their biological activities. However, antibodies have various problems such as less expression, low solubility, the use of animal cell-expressing cell lines, high costs in purification, and low stability in a reducing intracellular environment. Accordingly, non-antibody proteins that overcome the problems of antibodies and bind specifically to target molecules like the antibodies need to be urgently developed.

Peptides discovered by methods such as phage display and the like to be used for diagnosis and treatment of cancers or arteriosclerosis have limitations, such as low binding affinity, non-stability, and high immunogenicity. Accordingly, new technologies that can increase binding affinity and stability of an active peptide and decrease immunogenicity of the active peptide in vivo while overcoming such problems need to be developed.

SUMMARY

Therefore, the present inventors have found out that, when some human-derived proteins are selected and optimally modified and an active polypeptide is inserted thereinto, the active polypeptide exhibited superior properties, such as increased binding affinity or binding specificity, so that the active polypeptide can be used to substitute the existing peptide formulations and antibody formulations, based on which the present inventors completed the present invention.

Therefore, it is an object of the present invention to provide scaffold protein comprising an active polypeptide, the scaffold protein comprising: a) a polypeptide consisting of the $1^{st}$ to the $19^{th}$ amino acid residues of an amino acid sequence represented by SEQ ID NO: 1; b) a polypeptide including an active polypeptide; and c) a polypeptide consisting of the $29^{th}$ to the $86^{th}$ amino acid residues of the amino acid sequence represented by SEQ ID NO: 1, wherein said polypeptides are sequentially linked.

Another object of the present invention is to provide a polynucleotide encoding the scaffold protein.

Still another object of the present invention is to provide an expression vector comprising the polynucleotide.

Still another object of the present invention is to provide a host cell transformed with the expression vector.

Still another object of the present invention is to provide a method for preparing a scaffold protein comprising culturing the host cell.

Still another object of the present invention is to provide a composition for diagnosis comprising the scaffold protein as an effective ingredient.

Still another object of the present invention is to provide a pharmaceutical composition comprising the scaffold protein as an effective ingredient.

Still another object of the present invention is to provide a kit for diagnosis comprising the scaffold protein as an effective ingredient.

Still another object of the present invention is to provide a scaffold protein comprising an active polypeptide, the scaffold protein comprising: a) a polypeptide consisting of the $1^{st}$ to the $19^{th}$ amino acid residues of an amino acid sequence represented by SEQ ID NO: 1; b) a polypeptide including an amino acid sequence of activator protein 1 (AP-1) represented by SEQ ID NO: 3; and c) a polypeptide consisting of the $29^{th}$ to the $86^{th}$ amino acid residues of the amino acid sequence represented by SEQ ID NO: 1, wherein said polypeptides are sequentially linked thereto.

Still another object of the present invention is to provide a polynucleotide encoding the scaffold protein.

Still another object of the present invention is to provide a composition for diagnosis of cancers or arteriosclerosis, comprising the scaffold protein as an effective ingredient.

Still another object of the present invention is to provide a kit for diagnosis of cancers or arteriosclerosis, comprising the scaffold protein as an effective ingredient.

Still another object of the present invention is to provide a method for diagnosis, comprising the step of administering an effective amount of the scaffold protein to a subject in need thereof.

Still another object of the present invention is to provide a use of the scaffold protein for preparing a diagnostic agent.

Still another object of the present invention is to provide a method for diagnosis of cancers or arteriosclerosis, comprising the step of administering an effective amount of the scaffold protein to a subject in need thereof.

Still another object of the present invention is to provide a use of the scaffold protein for preparing a diagnostic agent of cancers or arteriosclerosis.

To achieve the above object, the present invention provides a scaffold protein comprising an active polypeptide, the scaffold protein comprising: a) a polypeptide consisting of the $1^{st}$ to the 19th amino acid residues of an amino acid sequence represented by SEQ ID NO: 1; b) a polypeptide including an active polypeptide; and c) a polypeptide consisting of the 29th to the 86th amino acid residues of the amino acid sequence represented by SEQ ID NO: 1, wherein the polypeptides are sequentially linked.

To achieve another object, the present invention provides a polynucleotide encoding the scaffold protein.

To achieve still another object, the present invention provides an expression vector comprising the polynucleotide.

To achieve still another object, the present invention provides a host cell transformed with the expression vector.

To achieve still another object, the present invention provides a method for preparing a scaffold protein comprising culturing the host cell.

To achieve still another object, the present invention provides a composition for diagnosis, comprising, as an effective ingredient, the scaffold protein.

To achieve still another object, the present invention provides a pharmaceutical composition, comprising, as an effective ingredient, the scaffold protein.

To achieve still another object, the present invention provides a kit for diagnosis, comprising, as an effective ingredient, the scaffold protein.

To achieve still another object, the present invention provides a scaffold protein comprising an active polypeptide, the scaffold protein comprising: a) a polypeptide consisting of the 1st to the 19th amino acid residues of an amino acid sequence represented by SEQ ID NO: 1; b) a polypeptide including an amino acid sequence of activator protein 1 (AP-1) represented by SEQ ID NO:3; and c) a polypeptide consisting of the 29th to the 86th amino acid residues of the amino acid sequence represented by SEQ ID NO: 1, wherein said polypeptides are sequentially linked.

To achieve still another object, the present invention provides a polynucleotide encoding the scaffold protein.

To achieve still another object, the present invention provides a composition for diagnosis of cancers or arteriosclerosis, the composition comprising, an effective ingredient, the scaffold protein.

To achieve still another object, the present invention provides a kit for diagnosis of cancers or arteriosclerosis, the kit comprising, as an effective ingredient, the scaffold protein.

To achieve still another object, the present invention provides a method for diagnosis, comprising administering the scaffold protein to a subject in need thereof.

To achieve still another object, the present invention provides a of the scaffold protein for preparing a diagnostic agent.

To achieve still another object, the present invention provides a method for diagnosis of cancers or arteriosclerosis, comprising the step of administering an effective amount of the scaffold protein to a subject in need thereof.

To achieve still another object, the present invention provides a use of the scaffold protein for preparing a diagnostic agent of cancers or arteriosclerosis.

BRIEF DESCRIPTION OF THE DRAWINGS

The patent or application file contains at least one drawing executed in color. Copies of this patent or patent application publication with color drawings will be provided by the office upon request and payment of the necessary fee.

DETAILED DESCRIPTION OF ILLUSTRATED EMBODIMENTS

Figure 1:
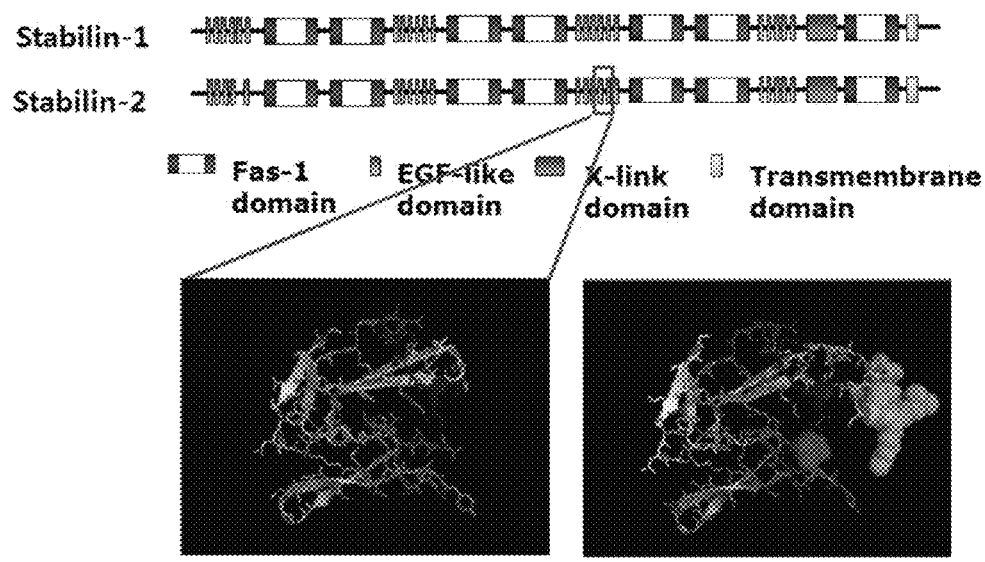
FIG. 1 shows a domain arrangement diagram of stabilin-2, and 3D modeling result images of the scaffold protein having an active peptide.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these exemplary embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements.

Active polypeptides refer to polypeptides that are contacted with target proteins to perform several actions, such as activation, deactivation, and phosphorylation of target proteins, and signaling. The scaffold protein of the present invention increases binding affinity or binding specificity of the active polypeptides to thereby increase activity of the active polypeptide.

Binding affinity refers to the strength of the binding between biomolecules. Binding specificity refers to the ability of a particular biomolecule to specifically bind to only a target molecule.

Hereinafter, the present invention will be described in detail.

The present invention provides a scaffold protein comprising an active polypeptide, the scaffold protein comprising:

a) a polypeptide consisting of the 1st to the 19th amino acid residues of an amino acid sequence represented by SEQ ID NO: 1;

b) a polypeptide including an active polypeptide; and c) a polypeptide consisting of the 29$^{th}$ to the 86$^{th}$ amino acid residues of the amino acid sequence represented by SEQ ID NO: 1, wherein said polypeptides are sequentially linked thereto and a polynucleotide encoding the scaffold protein.

The scaffold protein of the present invention is characterized by increasing binding affinity or binding specificity of an active polypeptide.

The scaffold protein (protein skeletal module) of the present invention refers to a protein structure that does not influence an in vivo immune system and can have an active polypeptide. The scaffold protein of the present invention needs to have superior in vivo activity due to a small molecular weight thereof, not influence activity of the embedded active polypeptide, not influence an in vivo immune system, and have no differences in individual effects or individual-specific effects due to its derivation from abundant proteins in vivo. The scaffold protein that has an active polypeptide to thereby improve stability and characteristics of the active polypeptide was first developed by the present inventors, and called Designed Modular Immunodiagnostics (DMID).

The active polypeptide of the present invention may have pharmaceutical activity, and the scaffold protein having an active polypeptide may exhibit pharmaceutical activity induced due to action of the active polypeptide. Therefore, the scaffold protein having an active polypeptide may have pharmaceutical activity of the active polypeptide, particularly enhanced pharmaceutical effects.

Preferably, the scaffold protein of the present invention may be designed based on a stabilin-2-derived polypeptide fragment. More preferably, the scaffold protein of the present invention may be a scaffold protein in which an active polypeptide is substituted or inserted in a region of an amino acid sequence represented by SEQ ID NO: 1, which does not influence a skeletal structure of the scaffold protein.

The scaffold protein according to an embodiment of the present invention was designed based on a stabilin-2 derived polypeptide fragment that is abundant in human beings. Stabilin-2, a transmembrane receptor, is involved in lymphocyte induction, cell adhesion, receptor scavenging, and angiogenesis. This protein has various domains, such as 7 fasciclin, 16 epidermal growth factor (EGF)-like domains, 2 laminin-type EGF-like domains, and a C-type lectin-like hyaluronan-binding link module.

Meanwhile, the present invention provides a polynucleotide encoding the scaffold protein.

The protein of the present invention is characterized by encoding a scaffold protein that increases binding affinity or binding specificity of an active polypeptide.

The polynucleotide of the present invention refers to a material that encodes a scaffold protein having an amino acid sequence represented by SEQ ID NO: 1 or having an amino acid sequence having 70% or higher homology to the amino acid sequence. Here, the polynucleotide may be DNA or RNA, and preferably may be DNA represented by SEQ ID NO: 2.

In addition, the present invention is characterized by providing an expression vector in which the polynucleotide of the present invention is inserted.

The expression vector of the present invention refers to an expression vector that is prepared by inserting the polynucleotide of the present invention into a vector following the method well known in the art to express the scaffold protein of the present invention through appropriate transcription/translation sequences.

The term "expression vector" of the present invention means a plasmid, a virus or other media, which are known in the art, into which the polynucleotide sequence encoding the protein of the present invention can be inserted or introduced. The polynucleotide sequence according to the present invention may be operably linked to an expression control sequence. The operably linked gene sequence and expression control sequence may be included in one expression vector having a selection marker and a replication origin together. As used herein, the term "operably linked" means that, when a proper molecule is linked to an expression control sequence, the gene sequence may be linked to the expression control sequence in a manner in which a gene can be expressed. The term "expression control sequence" means a DNA sequence that controls expression of an operably linked polynucleotide sequence in a particular host cell. Such an expression control sequence includes a promoter for transcription, any operator sequence for controlling transcription, a sequence for encoding a proper mRNA ribosomal binding site, and a sequence for controlling the termination of transcription and translation.

Examples of the expression vector, into which a polynucleotide encoding the scaffold protein of the present invention can be inserted, may include *E. coli* derived plasmids (pBR322, pBR325, pUC118, pUC119, pET30a, pET30c, and pGEX-GST) *Bacillus Subtilis* derived plasmids (pUBHO and pTP5), yeast derived plasmids (YEp13, YEp24, and YCp50), Ti plasmids, and the like. Animal viruses such as retrovirus, adenovirus, and vaccinia virus, insect viruses such as vaculovirus and the like, and plant viruses may be used. Binary vectors such as PZP, pGA and pCAMBIA may also be used. Those skilled in the art can select a vector suitable for introducing the polynucleotide sequence of the present invention. In the present invention, any vector that can introduce the polynucleotide sequence of the present invention into a host cell may be used. Preferably, a vector that is designed to facilitate induction of protein expression and separation of the expressed protein may be used. More preferably, a recombinant vector including the polynucleotide of the present invention, a pET32a vector, may be used.

Further, the present invention provides a host cell transformed with the recombinant expression vector of the present invention.

The transformed host cell may be a microorganism that is transformed with the recombinant expression vector of the present invention according to the method known in the art. The microorganism may be, but is not limited to, preferably *E. coli*, and more preferably *E. coli* BL21 or *E. coli* MC 1061.

As the method of transforming a host cell by introducing the recombinant vector according to the present invention thereinto, a calcium chloride (CaCl$_2$) and heat shock method, a particle gun bombardment method, a silicon carbide whisker method, a sonification method, an electroporation method, a precipitation method using polyethylenglycol (PEG), or the like, may be used, but is not limited thereto.

Various host-expression vector systems may be utilized to express the scaffold protein of the present invention. Such host-expression vector systems represent vehicles by which the coding sequences of interest may be produced and subsequently purified, and also represent cells in which may, when transformed or transfected with the appropriate nucleotide coding sequences, express the scaffold protein of the invention in situ. Such systems, include but are not limited to, microorganisms such as bacteria (e.g., *E. coli, B. subtilis*) transformed with recombinant bacteriophage DNA, plasmid DNA, or cosmid DNA expression vectors containing coding sequences of the scaffold protein of the Preetn invention; yeast (e.g., *Saccharomyces, Pichia*) transfected with recombinant yeast expression vectors containing a coding sequence of the scaffold protein; insect cell systems infected with recombinant virus expression vectors (e.g., baculovirus) containing the coding sequence of the scaffold protein; plant cell systems infected with recombinant virus expression vectors (e.g., cauliflower mosaic virus, CaMV; tobacco mosaic virus, TMV) containing the coding sequence of the protein skeletal protein or transformed with recombinant plasmid expression vectors (e.g., Ti plasmid) containing the coding sequence of the scaffold protein; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

The scaffold protein of the present invention is characterized by increasing binding affinity or binding specificity of the active polypeptide. The active polypeptide may be comprised by inserting a polynucleotide encoding the active polypeptide into a particular site of the scaffold protein. Further, the present invention provides an expression vector including a polynucleotide encoding the scaffold protein comprising an active polypeptide, and a host cell transformed with the expression vector.

The expression vector and the host cell are described as above.

The host cell may be E. coli.

Meanwhile, the present invention provides a method for preparing a scaffold protein comprising an active polypeptide, the method including culturing the host cell.

According to the method of the present invention, there can be efficiently produced scaffold protein comprising an active polypeptide, the active polypeptide having increased binding affinity or binding specificity.

With respect to the scaffold protein comprising an active polypeptide, which is prepared by the method of the present invention, its protein may be purified by any method known in the art, such as chromatography (e.g., metal-chelate chromatography, ion exchange chromatography, affinity chromatography, and size column chromatography, or the like), centrifugation, differential solubility, or any other standard method for protein purification.

The active polypeptide in the scaffold protein has higher binding affinity or is binding specificity to target protein than that of the active polypeptide alone.

Meanwhile, a label material or the like, which is used in the known detection methods, may be further attached to the scaffold protein of the present invention.

In addition, a material or the like effective for a binding target of the active polypeptide may be further attached to the scaffold protein of the present invention.

For example, polyethylene glycol (PEG), human serum albumin (HSA), Fc regions of antibodies, IgG molecules, cytotoxic drugs, radioactive isotopes, a contrast agent, a His-tag, biotin, a Flag-tag, nucleic acid, cytokine, or the like may be further attached to the scaffold protein of the present invention.

Therefore, the present invention provides a composition for diagnosis comprising an active polypeptide as an effective ingredient.

In addition, the present invention provides a method for diagnosis, comprising administering the scaffold protein comprising an active polypeptide to a subject in need thereof.

And the present invention provides a use of the scaffold protein comprising an active polypeptide for preparing a diagnostic agent.

As used herein, "effective amount" refers to an amount which exhibits the effect of diagnosing or treating, or providing the information for diagnosis or treatment by administering the composition or agent of the present invention in the subject in need thereof. And the "subject" refers to a mammal, preferably a human, and especially an animal comprising human and it also may be cells, tissues or organs originated from animals. The "subject" may be patient in need of diagnosis or treatment.

The inventive composition may comprise 0.001 to 99.999 wt % of the inventive composition and the residual content of a carrier.

A composition for diagnosis in the present invention comprises the scaffold protein comprising an active polypeptide as an effective ingredient.

Diagnosis in the present invention means that presence or absence, and progress of relevant diseases are determined based on the obtained results on presence or absence, distribution, quantity, and the like, of the target material of the active polypeptide.

For example, the IL-4 receptor is overexpressed in several human cancers (colorectal cancer, lung cancer, cervical cancer, and breast cancer). The scaffold protein having activator protein 1 (AP-1) of the present invention has binding strength to the IL-4 receptor, and thus is applicable to diagnosis and treatment of the cancers.

The methods of measuring the presence or absence, quantity, and/or pattern of the protein may include Western blot, enzyme linked immunosorbent assay (ELISA), radioimmunoassay, radioimmunodiffusion, Ouchterlony immunodiffusion, rocket immunoelectrophoresis, immunostaining of tissues, immunoprecipitation assay, complement fixation assay, fluorescence activated cell sorter (FACS), protein chip assay, and the like, but are not limited thereto.

The presence or absence, quantity, and/or pattern of the protein may be generally measured by detecting sizes and patterns of signals of detection labels linked to secondary antibodies.

Examples of the detection label may include enzymes, fluorescent materials, ligands, luminous materials, microparticles, redox molecules, radioisotopes, and the like, but are not limited thereto. When the enzyme is used as the detection label, a usable enzyme may be β-glucuronidase, β-D-glucosidase, β-D-galactosidase, urease, peroxidase or alkaline phosphatase, acetylcholine esterase, glucose oxidase, hexokinase and GDPase, RNase, glucose oxidase, luciferase, phosphofructokinase, phosphoenolpyruvate, carboxylase, aspartate amino transferase, phosphenolpyruvate cacarboxylase, β-lamatase, or the like, but is not limited thereto.

When the fluorescent material is used as the detection label, a usable fluorescent material may be fluorescein, isothiocyanate, rhodamine, phycoerytherin, phycocyanin, allophycocyanin, o-phthaldehyde, fluorescamin, or the like, but is not limited thereto. When the ligand is used as the detection label, a usable ligand may be a biotin derivative or the like, but is not limited thereto. When the luminous material is used as the detection label, a usable luminous material may be acrydinium ester, luciferin, luciferase, or the like, but is not limited thereto. When the mircroparticle is used as the detection label, a usable microparticle may be colloidal gold, colored latex, or the like, but is not limited thereto.

When the redox molecule is used as the detection label, a usable redox molecule may be ferrocene, a ruthenium complex, viologen, quinone, Ti ion, Cs ion, diimide, 1,4-benzo-quinone, hydroquinone, $K_4W(CN)_8$, $[Os(bpy)_3]^{2+}$, $[RU(bpy)_3]^{2+}$, $[MO(CN)_8]^{4-}$, or the like, but is not limited thereto.

When the radioisotope is used as the detection label, a usable radioisotope may be $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, $^{186}Re$, or the like, but is not limited thereto.

The composition for diagnosis of the present invention can give the findings of the presence or absence, distribution, amount, and the like of the active polypeptide, and provides information, based on which the presence or absence and progress of relevant diseases can be determined. The composition of the present invention is superior in sensitivity, precision, and accuracy of diagnosis as compared with a composition including an active polypeptide not embedded in the scaffold protein of the present invention.

Therefore, the present invention provides a kit for diagnosis, including, as an effective ingredient, the scaffold protein comprising an active polypeptide.

The kit for diagnosis may further include a support, a proper buffer, a secondary antibody labeled with a chromogenic enzyme or a fluorescent substance, a chromogenic substrate liquid, and the like. The support may be a nitrocellulose membrane, a 96-well plate synthesized by a polyvinyl resin, a 96-well plate synthesized by a polystyrene resin, a slide glass made of glass, or the like. The chromogenic enzyme may be peroxidase, alkaline phosphatase, or the like. The fluorescent substance may be FITC, RITC, or the like. The chromogenic substrate liquid may be 2,2'-azino-bis(3-ethyl-benzenzothiazoline-6-sulfonic acid) (ABTS), o-phenylenediamine (OPD), tetramethyl benzidine (TMB), or the like.

In addition, the present invention provides a pharmaceutical composition including, as an effective ingredient, the scaffold protein comprising an active polypeptide.

The pharmaceutical composition of the present invention can transfer a treatment material, a cytotoxic drug, and the like, which are effective for the binding target of the active polypeptide.

The pharmaceutical composition may target a different disease according to the type of the active polypeptide. For example, a pharmaceutical composition including, as an effective ingredient, a scaffold protein having AP-1 as the active polypeptide of the present invention, binds to the IL-4 receptor, which is overexpressed in several human cancers (colorectal cancer, lung cancer, cervical cancer, and breast cancer), and thus can transfer a treatment or a cytotoxic drug targeting the IL-4 receptor.

Therefore, the present invention provides a scaffold protein comprising AP-1, including:

a) a polypeptide consisting of $1^{st}$ to $19^{th}$ amino acid residues of an amino acid sequence represented by SEQ ID NO: 1;

b) a polypeptide including an amino acid sequence of AP-1 represented by SEQ ID NO: 3; and c) a polypeptide consisting of $29^{th}$ to $86^{th}$ amino acid residues of the amino acid sequence represented by SEQ ID NO: 1, wherein the polypeptides are sequentially linked.

Further, the present invention provides a polynucleotide encoding the scaffold protein comprising AP-1.

Preferably, the polynucleotide may be any one selected from the group consisting of a nucleic acid sequence of SEQ ID NO: 4 to SEQ ID NO: 6.

The active polypeptide refers to a polypeptide which is contacted with the target protein to perform several actions, such as signaling, and activation, deactivation, and phosphorylation of target proteins. Since cytokine IL-4 has an amino acid sequence binding to the IL-4 receptor, AP-1 itself has a binding strength to the IL-4 receptor. The IL-4 receptor has been known to be overexpressed in several human cancers (colorectal cancer, lung cancer, cervical cancer, and breast cancer), and thus the development of active polypeptides selectively binding to the IL-4 receptor may be applied to diagnose and treat the cancers. IL-4 is cytokine that increases cell adhesion. Since IL-4 causes arteriosclerosis, AP-1 peptides may be developed as a diagnosis agent and a treatment agent of arteriosclerosis.

Therefore, the present invention provides a composition for diagnosing cancers or arteriosclerosis, the composition including, as an effective ingredient, a scaffold protein having AP-1, and a kit for diagnosing cancers or arteriosclerosis, the kit including, as an effective ingredient, a scaffold protein having AP-1.

Further, the present invention provides a method for diagnosing cancers and arteriosclerosis, the method including administering a scaffold protein having AP-1 to a subject in need thereof.

Further, the present invention provides a use of a scaffold protein having AP-1, for producing a diagnostic agent of cancers or arteriosclerosis.

In the present invention, the cancers may be, not limited thereto, all type cancer changing the levels of biological substance having the binding affinity with AP-1 by incidence, progress, degeneration or extinction of cancer, and preferably may be colorectal cancer, lung cancer, cervical cancer, and breast cancer.

An inventive pharmaceutical composition may comprise the inventive scaffold protein or pharmaceutically acceptable salt thereof alone or further comprise pharmaceutically acceptable carriers, excipients, or diluents.

A pharmaceutically acceptable carrier, for example, carriers for the parenteral or oral preparations may be comprised. The carriers for the oral preparations may comprise lactose, starch, cellulose derivatives, magnesium stearate, stearic acid and the carriers for the parenteral preparations may comprise water, oil, saline, aqueous glucose and glycol. The examples of the stabilizers may be sodium hydrogen sulfite, sodium sulfite, and ascorbic acid. The examples of the preservatives may be benzalkonium chloride, methyl- or prophyl-paraben, and chlorobutanol. An inventive pharmaceutical composition may further comprise lubricants, humectants, sweeteners, flavors, emulsifiers, suspending solutions and etc., as well as the ingredient above. The list of pharmaceutically acceptable carriers is disclosed in Remington's Pharmaceutical Sciences, 19th ed., Mack Publishing Company, Easton, Pa., 1995.

The inventive pharmaceutical composition may be administered by any routes, for example, oral or parenteral routes. The parenteral routes comprise, not limited thereto, intravenous, intramuscular, intra-arterial, intra-marrow, intra pachymeninx, intra-cardiac, intradermal, subcutaneous, peritorial, intranasal, gastrointestinal tracts, sublingual, or rectal.

The inventive pharmaceutical composition may be formulated into reagent for oral administration or parenteral administration according to the mentioned above.

In case of the formulation for oral administration, the composition of the present invention may be formulated with a proper carrier for oral administration into powders, granules, tablets, pills, and sugar-coated tablets, capsules, liquids, gels, syrups, slurries, and emulsions by using the method known in the art. For examples of appropriate carriers, it may comprise sugars comprising lactose, dextrose, sucrose, sorbitol, mannitol, xylitol, erythritol and maltitol, starches comprising corn starch, wheat starch, rice starch and potato starch, celluloses comprising cellulose, methyl cellulose, sodium carboxymethylcellulose and hydroxypropylmethylcellulose, and fillers comprising gelatin and polyvinylpyrrolidone. And, if desired, it may comprise cross-linked polyvinylpyrrolidone, agar, alginic acid or sodium alginate as a solutionizer. Further, the inventive pharmaceutical composition may comprise an anti-coaglutinating agent, a lubricant, wetting agents, flavors, emulsifying agents, and antiseptics.

In case of parenteral administration, the inventive composition may be formulated into injections, creams, lotions, ointments, oils, humectants, gels, aerosols and nasal inhaler. These formulations are described in the *Remington's Pharmaceutical Science,* 15th Edition, 1975, Mack Publishing Company, Easton, Pa., which is well known in the pharmaceutical chemistry field.

Total effective amount of the inventive scaffold protein or pharmaceutically acceptable salt thereof may be administered to a patient with a single dose, or may be administered with multiple doses by fractionated treatment protocol. The pharmaceutical composition of the present invention may contain variable amount of effective ingredient according to the disease severity. The effective amount of the inventive scaffold protein or pharmaceutically acceptable salt thereof is preferably about 0.01 μg to 1,000 mg/kg body weight/day, more preferably 0.1 μg to 100 mg/kg body weight/day. However, the dose of the inventive scaffold protein or pharmaceutically acceptable salt thereof may be suitably determined by considering various factors, such as age, body weight, health condition, sex, disease severity, diet and excretion of a subject in need of treatment, as well as administration time and administration route. When those are considered, skilled person in the art may determine appropriate dose of the inventive scaffold protein for a certain use. The inventive pharmaceutical composition may not limit formulations, administration routes, and administration methods as long as they show the effect of the present invention.

The foregoing effects of the present invention are well shown in examples of the present specification.

In the examples of the present invention, a modular domain which has high affinity, a small molecular weight, and low immunogenicity and is abundant in human beings and of which a 3D structure can be verified was screened among many modular domains. An EGFL domain of Stamiin-2 was selected as the most suitable domain. The selected sequence was subjected to 3D modeling and in silico mutation, to thereby construct the most suitable model.

According to another embodiment of the present invention, a polynucleotide sequence encoding the selected scaffold protein was prepared and then introduced into an expression vector in which the polynucleotide can be expressed, which was then used to transform *E. coli*. The transformed strain was cultured to express the scaffold protein of the present invention, followed by extraction and purification.

In another embodiment of the present invention, the binding ability of the scaffold protein having AP-1 as the active polypeptide of the present invention was measured by surface plasmon resonance analysis. As the measurement result, when AP-1 is embedded in the scaffold protein of the present invention, the binding affinity of the scaffold protein was confirmed to be 174-fold higher than that of the naked AP-1 peptide.

In another embodiment of the present invention, a variation in detection sensitivity of the active polypeptide of the scaffold protein of the present invention was measured. As a result, when AP-1 is embedded in the scaffold protein of the present invention, the inhibitory effect on IL-4 activity of the scaffold protein was confirmed to be 10-fold higher than that of the naked AP-1 peptide.

In another embodiment of the present invention, diagnosis sensitivity by the scaffold protein having an active polypeptide of the present invention was measured. As a result of a cellular imaging or animal imaging experiment, when AP-1 is embedded in the scaffold protein of the present invention, the tumor targeting ability of the scaffold protein was confirmed to be further improved than the naked AP-1 peptide.

As set forth above, the present invention is directed to a novel scaffold protein which increases binding affinity or binding specificity of active polypeptides, and more particularly, to a scaffold protein including a polypeptide consisting of $1^{st}$ to $21^{st}$ amino acid residues of an amino acid sequence represented by SEQ ID NO:1; a polypeptide including an active polypeptide; and a polypeptide consisting of $29^{th}$ to $86^{th}$ amino acid residues of the amino acid sequence represented by SEQ ID NO:1, and a method for preparing the same. The scaffold protein of the present invention increases binding affinity or binding specificity of the active polypeptide, and thus is effective in diagnosis and treatment of diseases.

EXPERIMENTAL EXAMPLES

Example 1

Screening and Modeling of Designed Modular Immunodiagnostics (DMID) Candidates

<1-1> Screening 20 candidates were selected from modular domains which are present in large amounts out of protein domains expressed in human beings, through post-genomic screening for comparison and analysis with the human gene database, and then EGF-like (EGFL) domains were selected based on the conditions of a) high affinity, b) low molecular weight, c) low immunogenicity, d) abundance in human beings, and e) verifiability of the 3D structure.

The EGFL domain, which is a module composed of 40 amino acid residues, is present in a large number of plasma proteins and has a low molecular weight, high safety, and low immunogenicity. The EGFL domain has a simple structure with two β-sheets and three disulfide bonds, and its 3D structure is verifiable. Further, the EGFL domain has a loop which does not influence its structure, and thus facilitates insertion of active polypeptides. Therefore, the EGFL domain is appropriate as a DMID candidate.

<1-2> 3D Modeling

BLAST and AlignMaster programs were used for 3D modeling of the EGFL domain. The structure of the human EGFL domain was received from the Protein DataBank.

Knowledge based mutagenesis and 2D modeling were conducted by using nnPredic ((www.cmpharm.ucsf.edu/~nomi/nnpredict.html) and Jpred (http://www.compbio.dundee.ac.uk/~www-jpred/submit.html). Knowledge based 3-dimensional models was received from Swiss Model (http://www.expasy.ch/), followed by in silico mutagenesis and then verification with Chimera/Modeller 6. The last DMID model was analyzed and visualized by PyMOL.

Example 2

Expression and Purification of Recombinant DMID-AP1

<2-1> Preparation of Transformed Strain-Preparation of DMID-SalI-HindIII Cassette For preparation of the scaffold protein (DMID) of the present invention, the EGFL domain (4621-4869) present in the stabilin-2 protein was cloned into the BamHI and XhoI sites of pET-32a(+) (Novagen) which is an *E. coil* expression vector, thereby preparing an expression vector. The Sal1 restriction enzyme site was prepared by transgenesis of the EGFL domain from GCTGAC (4639-4644) into GTCGAC and the HindIII restriction enzyme site was prepared by transgenesis from AAAGCA (4703-4708) into AAGCTT, thereby preparing a DMID-Sal1-HindIII cassette into which active polypeptides can be inserted.

<2-2> Culture of Transformed Strain

The transformed Origami strain was cultured in a 20 ml tryptone phosphate (TP) broth (2% bacto-tryptone, 0.2% $Na_2HPO_4$, 0.1% $KH_2PO_4$, 0.8% NaCl, 1.5% yeast extract and 0.2% glucose) containing 50 µg/ml of Ampicillin and 25 µg/ml of Kanamycin overnight. The culture liquid was centrifuged at 4000×g for 5 minutes, and pellets were collected and then resuspended in the same volume of TP containing 50 µg/ml of Ampicillin. The resultant liquid was diluted with the TP broth by ten times, and was then cultured at 37° C. until the $OD_{600}$ value reached 0.5. The culture liquid after completion of culturing was cooled to 20° C., and then protein expression was induced with 0.2 mM IPTG (Isopropyl-β-D-thiogalactoside) for 12 hours. After that, cultured cells were collected and then stored at −80° C. prior to use.

<2-3> Extraction and Isolation-Purification of Protein

The stored cells were resuspended in 10 ml of 2×PBS containing 1 mM PMSF and 0.5 mM DTT, and then ultrasonicated under the conditions of duty cycle: 30% and output: 2.5 for 5 min. The crushed cells were centrifuged at 15,000 g for 10 minutes, and then the supernatant was taken.

The collected supernatant was loaded on the Ni-NTN column (amersham pharmacia biotech AB, Vt=0.5 ml)) equilibrated with the 2×PBS buffer and set according to the manufacturer's manual. Since the DMID labeled with the 6×(His)-tag was attached on the column, the column was washed with the 2×PBS buffer containing 30 mM imidazole (10 folds of the column volume), and then proteins adhering to the column were collected by using the 1×PBS buffer (elution buffer) containing 250 mM imidazole.

Example 3

Verification on Improvement in Binding Ability of Recombinant DMID-AP1—Surface Plasmon Resonance Analysis In order to verify the biding ability of the scaffold protein having AP1 of the present invention (DMID-AP1), binding constants of naked AP1 and DMID-AP1 were measured by using the Biacore 2000 through surface plasmon resonance analysis. An ectodomain of the human IL-4 receptor (IL-4Ra), which was expressed in insect cells (SF21) and purified, was diluted in the HBS buffer (10 mM HEPES, pH 7.4, 150 mM NaCl, 3.4 mM EDTA, and 0.005% surfactant P20), and then coated on a surface of the Biacore CM5 chip according to the manufacturer (Biacore Inc.)'s manual (2500 RU). The AP-1 peptide or DMID-AP1 diluted with the same buffer was allowed to flow (50 ul/min), to measure a variation in the RU value, and then the Biaevaluation 2.0 (program) was used to obtain the binding constant.

Figure 2:
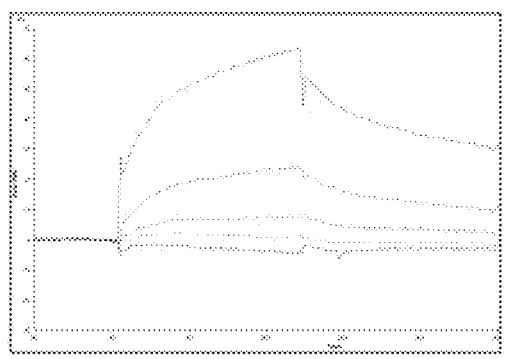
FIG. 2 shows surface plasmon resonance experiment result graphs (DMID AP-1: scaffold protein having AP-1 of the present invention, Peptide AP-1: AP-1 peptide not binding to scaffold protein, Negative control: negative control).
Figure 2:
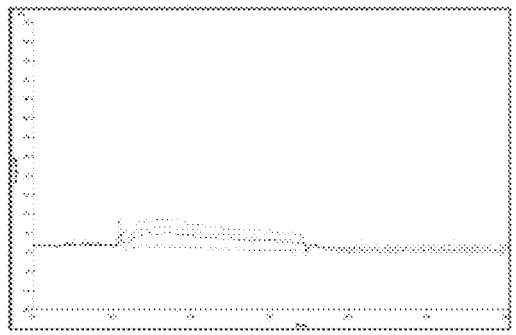
Figure 2:
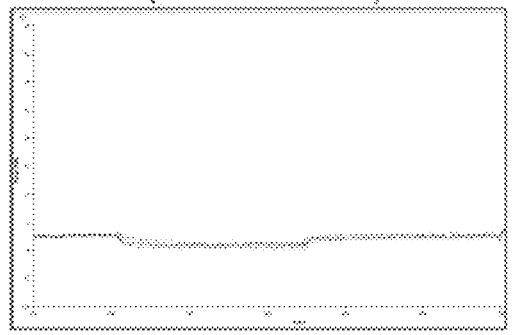
Figure 3:
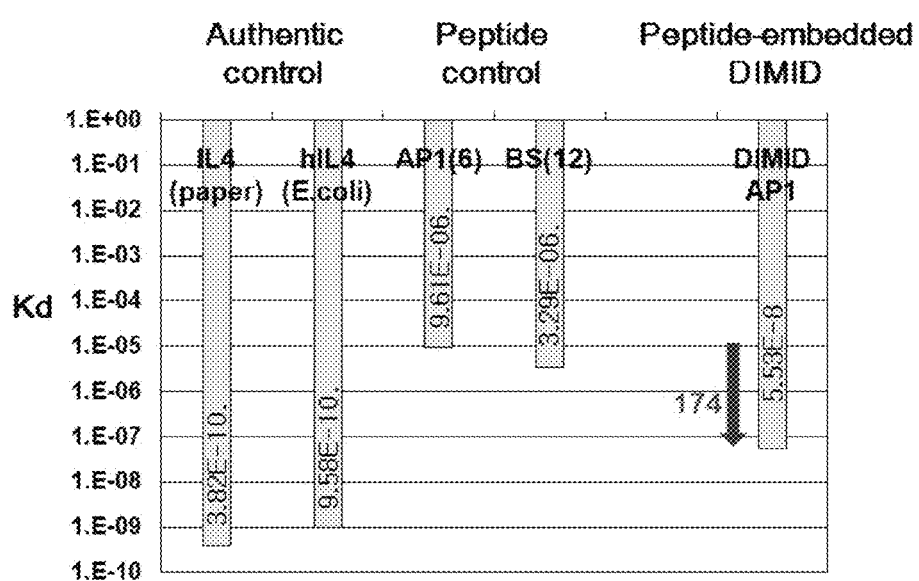
FIG. 3 shows a graph comparing binding constants measured as surface plasmon resonance experiment results (authentic control: binding constant of IL-4, peptide control: binding constant of AP-1 peptide not binding to scaffold protein, Peptide-embedded DMID: binding constant of scaffold protein comprising AP-1).

As shown in FIG. 2 and FIG. 3, the result of surface plasmon resonance analysis confirmed that the affinity of the peptide embedded DMID was 174 fold higher than that of the naked peptide.

Example 4

Verification 1 on Improvement in Detection Ability of Recombinant DMID-AP1—Measurement of Degree of Inhibition on Activity of IL-4 Receptor $5 \times 10^5$ THP1 cells (NIH AIDS Research and Reference Reagent Program, NCI9949) were seeded on a 6-well plate, and then treated with 1000 ng/ml of phorbol12-myristate13-acetate (PMA) (Sigma, P8139-1MG) for three days to implement cell activation. The cells were cultured in serum-free conditions for 18 hours, and then 0.67 nM (1×) of IL-4 alone or together with various concentrations of [$10^n \times (0.67$ nM)] of the AP-1 peptide or recombinant DMID-AP1 was treated. The phosphorylation of the Stat protein induced by the binding between IL-4 and the IL-4 receptor was measured by using rabbit polyclonal antibody anti-STAT6 (Cell Signaling, #9362) and rabbit polyclonal antibody anti-pTyr641-STAT6 (Cell Signaling, #9361) through the Western blot.

Figure 4:
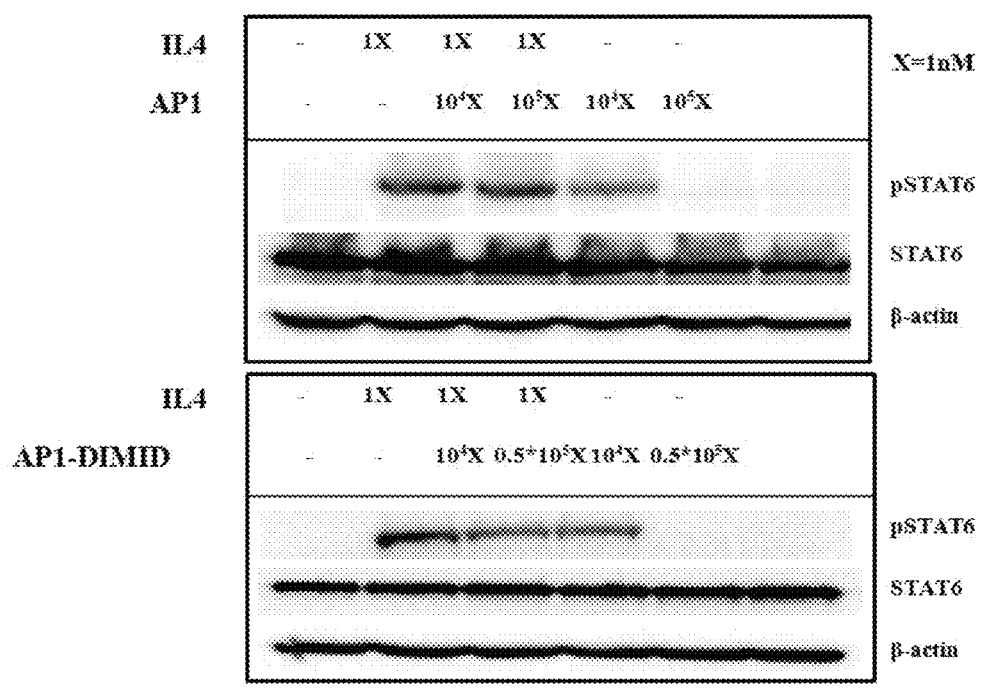
FIG. 4 shows experiment result images obtained by measuring an inhibitory effect of the scaffold protein comprising AP-1 of the present invention on signaling of the IL-receptor (IL4: interleukin 4, AP1: AP1 not binding to scaffold protein, AP1-DIMID: AP1 binding to scaffold protein, STAT6: level of STAT6, pSTAT6: level of phosphorylated STAT6).

As a result, as shown in FIG. 4, it was confirmed that DMID-AP1 of the present invention was 10 times or higher than AP-1 in view of the degree of inhibition on IL-4 activity to phosphorylate the Stat protein than AP1.

Example 5

Verification 2 on Improvement in Detection Ability of Recombinant DMID-AP1—Cellular Imaging, Animal Imaging <5-1> Cellular Imaging In order to find out the competitive binding ability of the scaffold protein comprising AP-1 (DMID-AP1) with the IL-4 receptor expressed in cells, the binding abilities of naked AP1 and DMID-AP1 to the IL-4 receptor were measured by using the fluorescence-labeled protein. The AP-1 peptide or the purified DMID-AP1 was dialyzed with a dialysis buffer (50 mM Boric acid, 150 mM NaCl, 1 mM EDTA, pH 9.0) at 4° C., and then allowed to react with a fluorescent material, fluorescein Isothiocyanate (FITC) (sigma), at 37° C. for 1 hour, thereby being labeled. The reaction was stopped by an addition of 50 mM glycine at 37° C. for 5 minutes, and then dialysis using a dialysis buffer (20 mM Tris HCl, pH 8.0) was conducted at 4° C. The same amounts of peptide, AP-1, and DMID-AP1 were added to H226 cells, followed by binding and washing, and then fixed with 4% paraformaldehyde (PFA). Cell nuclei were stained with 4',6-diamidino-2-phenylindole (DAPI) and then observed by a fluorescence microscope (Zeiss, Oberkochen, Germany).

Figure 5:
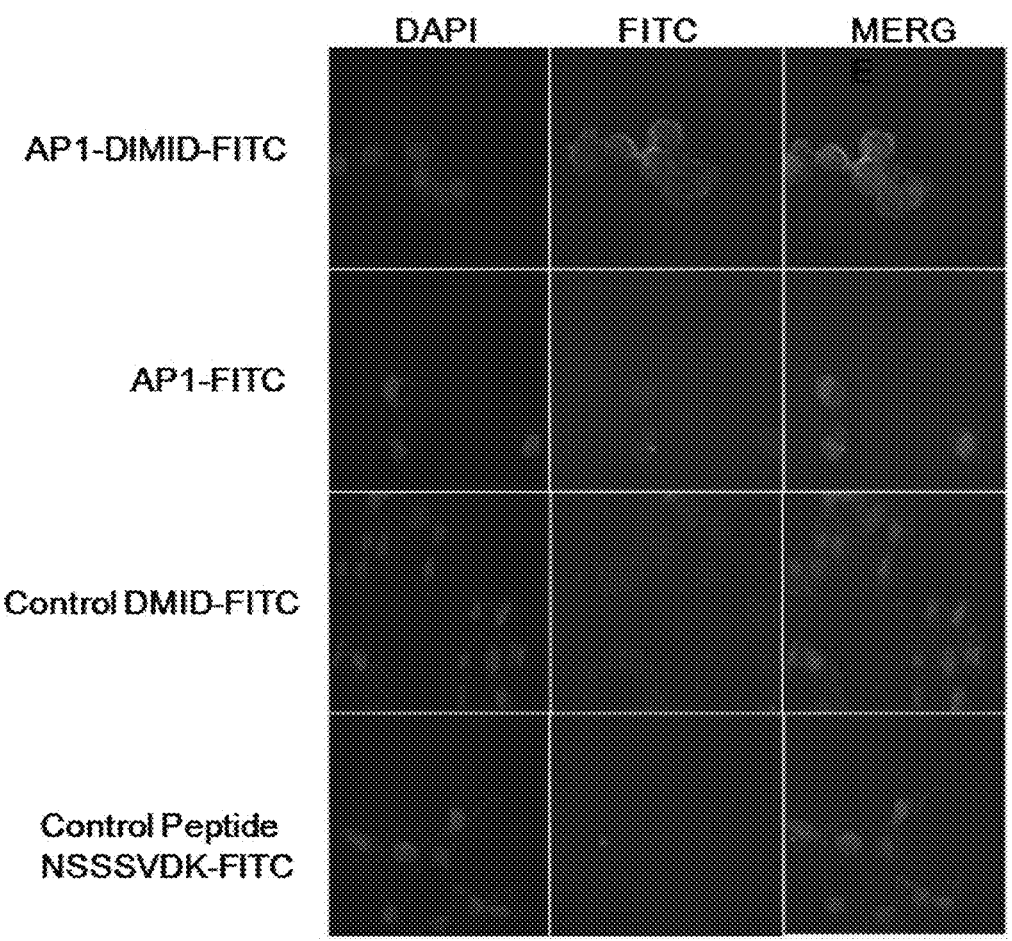
FIG. 5 shows cellular imaging experiment result images obtained by measuring improvement in detection ability of the scaffold protein comprising AP-1 of the present invention (DAPI: image in which cell nucleus was stained with 4',6-diamidino-2-phenylindole (DAPI), FITC: image in which scaffold protein was labeled with Fluorescein Isothiocyanate, MERGE: image in which DAPI and FITC images are composed, AP1-DIMID-FITC: AP1 binding to scaffold protein, labeled with FITC, AP1-FITC: AP-1 labeled with FITC, Control DMID-FITC: scaffold protein not having AP-1, labeled with FITC, NSSSVDK: control peptide in which peptide of sequence was labeled with FITC).

As a result, as shown in FIG. 5, it was confirmed that AP1-DMID-FITC had superior ability over AP-1 or control peptides in view of labeling cells expressing the IL-4 receptor.

<5-2> Animal Imaging $1 \times 10^7$ H226 cells were floated in a culture medium, and then subcutaneously injected to the right femoral region of a 5-6 week-age female BALB/c nude mouse, thereby preparing a subcutaneous tumor model. After 3 weeks, the mouse was used when the tumor size was 0.1~1 cm. The tumor-transplanted mouse was anesthetized, and then, 150 µg of the AP-1 peptide or the DMID-AP1, to which a fluorescent material was bound, was intravenously injected to the tail region thereof. The tumor targeting function of the fluorescence-labeled peptide was analyzed by using optics.

Figure 6:
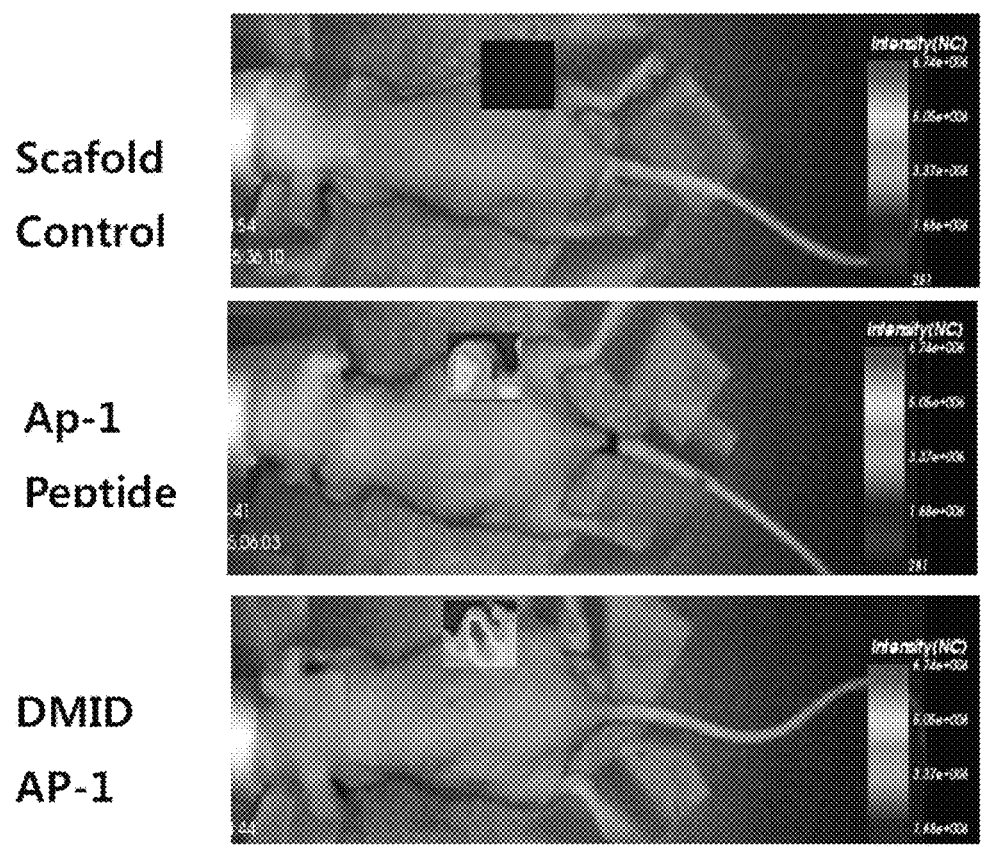
FIG. 6 shows animal imaging experiment result images obtained by measuring improvement in detection ability of the scaffold protein comprising AP-1 of the present invention (Scaffold control: mouse injected with scaffold protein not having AP-1, AP-1 Peptide: mouse injected with AP-1 peptide, DMID AP-1: mouse injected with DMID AP-1).

As a result, as shown in FIG. 6, it was confirmed that the tumor targeting function of DMID-AP1 was further improved than that of AP-1.

What is claimed is:

1. A scaffold protein comprising an active polypeptide, the scaffold protein comprising:
   a) a polypeptide consisting of the 1st to the 19th amino acid residues of an amino acid sequence represented by SEQ ID NO: 1;
   b) a polypeptide including an active polypeptide; and
   c) a polypeptide consisting of the 29th to the 86th amino acid residues of the amino acid sequence represented by SEQ ID NO: 1,
   wherein the polypeptides are sequentially linked.

2. A composition for diagnosis comprising the scaffold protein of claim 1 as an effective ingredient.

3. A pharmaceutical composition comprising the scaffold protein of claim 1 as an effective ingredient.

4. A kit for diagnosis comprising the scaffold protein of claim 1 as an effective ingredient.

5. A scaffold protein comprising an active polypeptide, the scaffold protein comprising:
   a) a polypeptide consisting of the 1st to the 19th amino acid residues of an amino acid sequence represented by SEQ ID NO: 1;
   b) a polypeptide including an amino acid sequence of activator protein 1 (AP-1) represented by SEQ ID NO:3; and
   c) a polypeptide consisting of the 29th to the 86th amino acid residues of the amino acid sequence represented by SEQ ID NO: 1,
   wherein the polypeptides are sequentially linked.

6. A composition for diagnosis of cancers or arteriosclerosis, comprising the scaffold protein of claim 5 as an effective ingredient.

7. A kit for diagnosis of cancers or arteriosclerosis, comprising the scaffold protein of claim 5 as an effective ingredient.

* * * * *